United States Patent [19]

Cheung

[11] Patent Number: 5,132,242
[45] Date of Patent: Jul. 21, 1992

[54] FLUORESCENT MICROSPHERES AND METHODS OF USING THEM

[76] Inventor: Sau W. Cheung, 8528 Douglas Ct., St. Louis, Mo. 63144

[21] Appl. No.: 434,892

[22] Filed: Nov. 13, 1989

Related U.S. Application Data

[63] Continuation-in-part of Ser. No. 73,770, Jul. 15, 1987, abandoned.

[51] Int. Cl.$^5$ .......................................... G01N 33/547
[52] U.S. Cl. ..................... 436/501; 436/503; 436/532; 436/533; 436/546; 436/800; 436/805; 436/823
[58] Field of Search ............. 435/7.5, 6; 436/533, 436/800, 501, 503, 532, 546, 805, 823

[56] References Cited

U.S. PATENT DOCUMENTS

| | | | |
|---|---|---|---|
| 3,853,987 | 12/1974 | Dreyer | 424/1 |
| 4,035,316 | 7/1977 | Yen et al. | 436/546 |
| 4,105,598 | 8/1978 | Yen et al. | 521/53 |
| 4,108,972 | 8/1978 | Dreyer | 421/1 |
| 4,140,662 | 2/1979 | Reckel et al. | 436/533 |
| 4,224,198 | 9/1980 | Rembaum et al. | 424/12 |
| 4,326,008 | 4/1982 | Rembaum | 428/403 |
| 4,582,810 | 4/1986 | Rosenstein | 436/533 |

FOREIGN PATENT DOCUMENTS 1124643  6/1982  Canada.

OTHER PUBLICATIONS

Cheung et al, Cell Biology International Reports, vol. 1, No. 3, 1977, pp. 255-262.
Klausner et al, Bio/Technology, Aug. 1983, pp. 471-478.
Nairn (ed), Fluorescent Protein Trancing, Churchill Livingstone Ltd, 1976, pp. 5-38, 68-107 and 369-372.
Muirhead et al, Bio/Technology, vol. 3, Apr. 1985, pp. 337-356.
R. S. Molday, W. J. Dreyer, A. Rembaum, and Yen, Journal of Cell Biology, vol. 64, 1975, pp. 75-88.
Kaplan et al, Biochimica et. Biophysica Acta, vol. 728, 1983, pp. 112-120.
Parks et al, Genetics, vol. 76 No. 4, Apr. 1979 pp. 1962-1966.
Fuccillo, Bio Techniques, vol. 3, No. 6, 1985, pp. 494-501.
Fornusek et al, CRC Critical Reviews in Therapeutic Drug Carrier Systems, vol. 2, Issue 2, 1986 pp. 137-174.
Rembaum and Dreyer, Science, vol. 208, 25 Apr. 1980, pp. 364-368.
Feinberg et al, Analytical Biochemistry 132, 1983, pp. 6-13.
Harper et al, Chromosoma, 83, 1981, pp. 431-439.
March, Advanced Organic Chemistry: Reactions, Mechanisms and Structure, Mc Graw-Hill, NY., 2nd edition, 1977, pp. 386-387.
Cheung et al, (abstract) Annual Meeting, American Society of Human Genetics, San Diego, Oct. 19-22 1977.
Cheung et al, Advances in Gene Technology: The Molecular Biology of Development, ICSU Short Reports vol. 7, 1987, p. 123.

*Primary Examiner*—Mary E. Ceperley
*Attorney, Agent, or Firm*—Polster, Lieder, Woodruff and Lucchesi

[57] ABSTRACT

Highly fluorescent latex microspheres have a diameter of less than five hundred angstroms and have more than five thousand fluorescent markers per sphere. The microspheres are prepared by reacting an acrylic latex bead with a diamine and a fluorescent amine at elevated pH to attach a spacer arm and a marker, respectively, to the bead by transacylation of ester terminations on the surface of the bead. A protein such as avidin or an immunoglobulin may then be conjugated to the spacer arm. A single fluorescent microsphere is visible using standard fluorescent microscopy. Therefore the microspheres may be utilized not only to visualize cell surface antigens but also DNA encoding for single genes, by means of a biotinylated DNA probe.

15 Claims, 1 Drawing Sheet

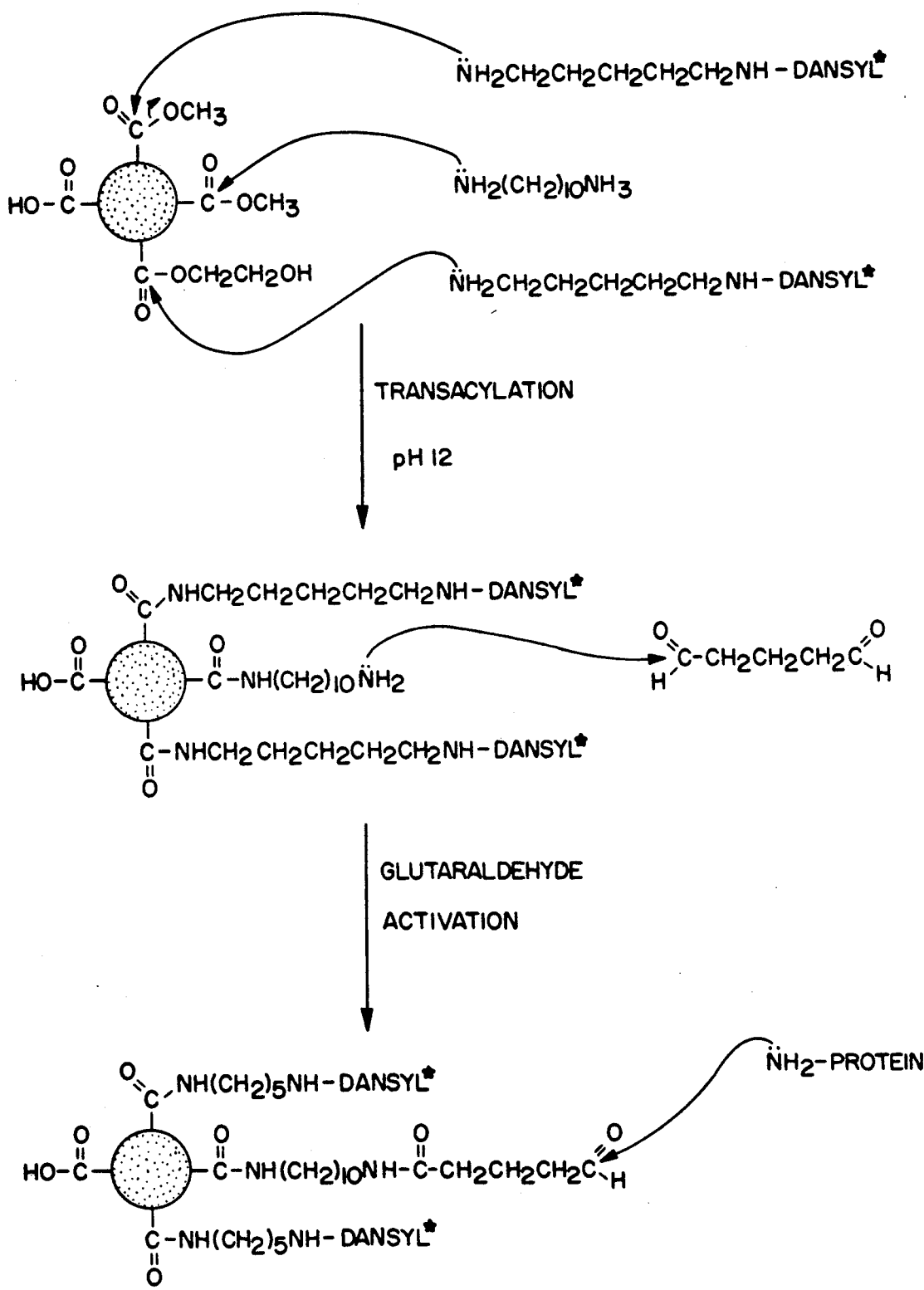

FLUORESCENT MICROSPHERES AND METHODS OF USING THEM

CROSS-REFERENCE TO RELATED APPLICATIONS

This application is a continuation-in-part of copending application Ser. No. 07/073,770, filed Jul. 15, 1987, abandoned.

BACKGROUND OF THE INVENTION

This invention relates to microspheres and particularly to fluorescent microspheres and methods of making and using them. Fluorescent microspheres have long been known, but their use has been limited by the complexity of making them, their limited visibility, the limited stability of some forms of them, their tendency to clump together, the lack of sensitivity of procedures using them, and their tendency to produce a large background fluorescence which makes visualization difficult and causes diagnostic error.

Biochemical probes have found widespread use in biochemistry and medicine. A popular review of these technologies is found in Klausner and Wilson, "Gene Detection Technology Opens Doors for Many Industries," *Bio/Technology*, August 1983, pp. 471-478. The most popular of these probes include a radioactive tracer, or an enzyme which catalyzes color-producing reactions, or a fluorescent species (fluorochrome) which fluoresces brightly under light of the appropriate wavelength. As set out in that article, some of these techniques presently permit detection of as few as $10^4$ copies of a single gene, although the techniques require several processing steps and several hours to carry out.

Radioactive probes create substantial handling and waste disposal problems, and color-forming enzymes are insensitive and hence require a large sample of the substrate to visualize.

Fluorochrome labels have now found wide use in microbiology. They are particularly useful in localizing cell surface antigens and in detecting specific nucleic acid sequences, although their usefulness is by no means limited to these applications. Two well-known methods of detecting fluorochrome-labeled species are fluorescence microscopy, described for example in Fluorescent Protein Tracing, ed. by R. C. Nairn, especially Chapter 4 (Churchill Livingstone Ltd. 1976), and flow cytometry, described for example in Muirhead et al., Bio/Technology, 3, pp. 337-356 (1985).

Direct staining with fluorescently-labeled antibodies produces a weak signal which is difficult to detect and presents several other difficulties, such as the complication of the procedure and its tendency to inactivate the antibody during attachment of the fluorescent marker. These difficulties are partially overcome by a sandwich technique in which a fluorescent marker is attached to a secondary antibody that in turn binds to a specific primary antibody. The lack of efficiency and specificity of the secondary binding, however, introduces new problems with this type of indirect method.

A "fluorescent vehicle" for attachment as a visible marker to an IgG fraction of secondary antibody was developed by Molday, Dreyer, Rembaum, and Yen, *Journal of Cell Biology*, 64, pp. 75-88 (1975). By emulsion copolymerization they synthesized latex microspheres having a diameter from 300 angstroms to 3400 angstroms. These microspheres are designed to be attached to a substrate, namely cell surface antigens to which primary antibodies have been attached, via secondary antibodies bound to the spheres. The spheres may be visualized via electron microscopy or by the addition to the spheres of radioactive or fluorochrome probes. The microspheres contain about 57% methyl ester terminations, about 30% hydroxyethyl ester groups, and about 10% carboxylic acid groups. Fluorescent species were attached to some of these microspheres, having a diameter of 600 angstroms, through the hydroxyethyl ester groups via a cyanogen the carboxylic acid groups. The spheres had limited fluorescence and tended to clump into large aggregates. The spheres were used in an indirect method of localizing cell surface antigens. Variations of these spheres are described in U.S. Pat. Nos. Dreyer, 3,853,987, Yen et al., 4,035,316, Yen et al., 4,105,598, Dreyer, 4,108,972, Rembaum et al., 4,224,198, and Rembaum et al. 4,326,008.

Kaplan et al., *Biochimica et Biophysica Acta*, 728, pp. 112-120 (1983) modified the Molday et al. technique and synthesized 500 angstrom diameter microspheres containing a fluorescent cross-linking agent, fluorescein. This technique allowed them to incorporate 700 fluorescein molecules per microsphere and reduced background fluorescence. The fluorescent microspheres were then conjugated to acetylated avidin which binds to biotinylated monoclonal antibody using both the sandwich method and direct detection of surface antigens. This involves several steps in addition to the synthesis of fluorescent microspheres, including acetylation of avidin, purification of monoclonal antibody and biotinylation of monoclonal antibody. However, this technique demonstrated the fact that fewer than ten thousand receptors per cell can be detected by fluorescent flow cytometry. These workers suggested the use of larger spheres, which enable them to attach more fluorochrome and thereby enhance the fluorescent signal, to detect cells containing even fewer receptors. Such an approach would also decrease sensitivity because of steric hindrance.

Parks et al., *Proc. Natl. Acad. Sci. (USA)*, 76, pp. 1962-66 (1979), using 0.783 micrometer (7830 angstrom) fluorescent microspheres, showed that as few as some tens of microsphere-antigen conjugates per cell could be used to select hybridomas from mixtures. These authors report that individual beads were visible under laser excitation.

Fuccillo, *BioTechniques*, 3, pp 494-501 (1985) describes other uses of the avidin-biotin complex.

Fornusek and Vetvicka, "Polymeric Microspheres as Diagnostic Tools for Cell Surface Marker Tracing," in *CRC Critical Reviews in Therapeutic Drug Carrier Systems*, 2, pp. 137-174 (1986), includes an extensive review of the use of microspheres, including fluorescent microspheres, for cell surface marking. These authors point out that, "Despite all the progress it has brought to cell biology, the fluorescence detection of cell surface markers is relatively tedious and rather insensitive with respect to the recent applications of it." These authors utilize fluorescent microspheres which are on the order of 20,000 angstroms, and cite others who utilize microspheres (Covaspheres TM) of about 7,000 to 9,000 angstroms in diameter to make the microspheres individually observable.

SUMMARY OF THE INVENTION

One of the objects of this invention is to provide a method of forming microspheres which have a far greater degree of fluorescence than previously known fluorescent microspheres.

Another object of this invention is to provide such microspheres which may be individually observable by either manual or automated fluorescence microscopy, but which are quite small.

Another object of this invention is to provide such microspheres which do not have a tendency to clump and which will remain in single suspension and will react individually with substrates.

Another object of this invention is to provide such microspheres which provide a sharp contrast between background and the substrate to which they are bound.

Another object is to provide methods of using such microspheres to increase the sensitivity and resolution of known fluorescence microscopy and flow cytometry procedures and to detect features of substrates which heretofore were not detectable, such as precise topological resolution of antigenic sites and rapid, high-resolution mapping of single gene sequences.

Other objects of this invention will be apparent to those skilled in the art in light of the following description and accompanying drawings.

In accordance with one aspect of this invention, generally stated, a method of forming a fluorescent bead is provided which comprises simultaneously reacting an acrylic latex bead with a fluorescent amine and with an amine-terminated spacer to form a conjugate of the fluorescent amine and the spacer diamine with the bead, and thereafter a step of separating the bead from unconjugated fluorescent amine and unconjugated spacer. The method is preferably carried out at a high pH, most preferably a pH of 11 to 13.5. Under these reaction conditions, substantially all the ester groups can be replaced by forming covalent bonds with the amine moieties through a transacylation reaction. Such transacylation reactions are described in March, Advanced Organic Chemistry: Reactions, Mechanisms, and Structure, 2nd edition 1977, pp. 386-87, and in Beckwith, Synthesis of amides, pp 96-105 (in Zabicky, The chemistry of amides (Interscience 1970)). As set out in these reference, the conversion of esters to amides is a useful reaction, and unsubstituted, N-substituted, and N,N-disubstituted amides can be prepared in this way from the appropriate amine. The unreacted bead is chosen to have several thousand ester terminations on its surface, preferably over ten thousand. Processes for forming such beads are well known in the art. The processes of the Molday et al. paper, supra, Rembaum et al. U.S. Pat. Nos. 4,224,198, Yen et al., 4,105,598, and Rembaum, 4,326,008 are particularly preferred. As described in these sources, the size of their acrylic beads is controlled by the relative amount of water to monomers, and by the relative amounts of surfactant and initiator to monomers utilized. The ester group may be alkyl or aryl, although for convenience the ester group will generally be alkyl and hydroxyalkyl esters containing from one to five carbon atoms.

The spacer is preferably a diamine, most preferably a straight chain aliphatic diamine having a length of from eight to twenty carbon atoms. A protein, such as avidin or an immunoglobulin, is conjugated to the free end of the diamine. The fluorescent amine is preferably a straight chain aliphatic having a length of from three to seven carbon atoms and a fluorescent dansyl moiety, but any fluorochrome with a primary amino group may be attached to the spheres. Preferably, the fluorescent amine and the diamine are present in the reaction in a ratio of from three to five parts of fluorescent amine to one part diamine. Because the fluorescent amine and the diamine react competitively for all the ester terminations on the surface of the bead, a far greater number of fluorescent markers may be attached to the bead, and the relative number of fluorescent markers and spacers may be controlled simply by their relative abundance (and reactivity with the ester terminations) in the reaction mixture, rather than by the relative number of different terminations on the beads. The chemical composition of the acrylic latex bead is also far less critical than in the fluorescent beads of Molday et al. Moreover, because the reaction is not believed to affect carboxylic acid terminations on the beads, the hydrophilic character of the beads is not spacers.

The latex bead of the invention is preferably made by a modification of the methods of Molday et al., supra. Any of the methods of the Molday et al. workers, patents cited supra may be utilized to form the beads, so long as beads which are sufficiently small and which have sufficient numbers of ester terminations are formed. The untreated beads are preferably made by suspension copolymerization of acrylic (including methacrylic) monomers, at least some of which are hydroxy or carboxy terminated to make the beads hydrophilic. The untreated bead preferably has both alkoxy groups and alkoxy alcohol groups, both of which react with the fluorescent amine and the diamine reactants. In this way, a far greater percent of the bead is covered with fluorescent moieties than in the Molday et al. procedure, and the relative amounts of fluorescent amine markers and diamine attachment points is controlled more precisely.

By carrying out the reaction of the beads with the spacers and fluorescent amines in a dilute suspension, clumping of the beads is greatly reduced.

The microsphere of the present invention is a latex bead having a diameter of less than 500 angstroms and having conjugated to its surface at least 5,000 fluorescent molecules. A plurality of these beads may be used as a marker system of great sensitivity and precision. The beads are preferably acrylic beads having a diameter of from 200 to 400 angstroms and preferably have in excess of 10,000 fluorescent molecules conjugated per bead. Preferably, a protein such as avidin or an immunoglobulin is conjugated to the bead through a spacer containing a chain of from eight to twenty carbon atoms. The fluorescent molecule is preferably conjugated to the bead through an amine linkage and a straight chain aliphatic having a length of from three to seven carbon atoms.

The intensely fluorescent, approximately 300 angstrom diameter microsphere of the invention may be utilized in either manual or automated fluorescence microscopy to determine the precise location of the binding site of the microsphere on a substrate (biological analyte). For example, at a magnification of 2500×, under ultraviolet light, individual microspheres of the preferred embodiment are easily visible, emitting light at 430 mu and 525 mu. At this magnification, the location of a microsphere adhered to a human chromosome may easily be determined. At a magnification of 26,800×, electron photomicrographs of the microspheres show their location on DNA-biotin-avidin-microsphere complexes.

The microspheres may further be utilized for screening tests without the use of either UV light sources or microscopy. For example, microspheres of the invention marked with rhodamine B markers and carrying antibodies on its spacers have been found to be visible under normal light.

Other aspects of the invention will best be understood in light of the following description of the preferred embodiments.

BRIEF DESCRIPTION OF THE DRAWINGS

In the drawings, the FIGURE is a diagrammatic representation of a method of forming a fluorescent bead in accordance with the present invention.

DESCRIPTION OF THE PREFERRED EMBODIMENT

The following examples are illustrative of the preferred methods and microspheres of the present invention but are not in limitation of the broader aspects of the invention.

EXAMPLE 1

Production of Microspheres

Latex microspheres having a mean diameter of 300 angstroms were prepared by a modification of the emulsion polymerization method of Molday, et al., *Journal of Cell Biology*, 64, pp. 75–88 (1975). Briefly, four acrylic monomers obtained from Fluka Chemical Company were purified in the following manner:

2-Hydroxyethyl methacrylate (HEMA)—distilled in the presence of a 2% hydroquinone at 76° C., 1.1 mm Hg pressure.

Methyl methacrylate (MMA)—distilled in the presence of a 0.5% hydroquinone at 57° C., 150 mm Hg pressure.

Methylacrylic acid (MAA) distilled with 0.05% hydroquinone at 63° C., 10 mm Hg pressure.

Ethylene glycol dimethacrylate (EGD)—distilled with 2% hydroquinone at 86° C. and 1.1 mm Hg pressure.

A suspension of microspheres was made by adding 0.9 parts by weight of HEMA, 1.71 parts of MMA, 0.3 parts MAA, 0.09 parts EGD, 0.120 parts of sodium dodecyl sulfate (SDS- an emulsifying agent), and 0.013 parts of ammonium persulfate (AP- a cross-linking agent) to 100 parts of distilled water. The emulsion was rotated in a specially constructed tumbling container at 98° C., under argon gas for 1 hour. Emulsifier and other ionic impurities were removed from the resultant suspension by dialysis in an Amicon ultrafiltration chamber until the conductivity of the filtrate was less than 5 umho.

The synthetic microspheres were examined by transmission electron microscopy. They appeared as uniformly round bodies ranging from 200 to 400 angstroms in diameter. The presence of hydroxyethyl ester, carboxy, and methyl ester functional groups enables molecules containing primary amino groups to be covalently bonded to the microspheres by an assortment of chemical reactions. The resulting 300 angstrom diameter spheres have surfaces containing about 10% carboxylic acid terminations, about 30% hydroxyethyl ester terminations, and about 57% methyl ester terminations.

EXAMPLE 2

Production of Fluorescent Microspheres

The acrylic latex spheres of Example 1 were provided both with fluorescent markers and with spacers in a single reaction mixture by reacting not only the methyl ester groups but also the hydroxyethyl ester groups with a mixture of 80% dansylcadaverine (1-dansyl, 1,5-diamino pentane) and 20% 1,12-diaminododecane. A mixture of 30 mg of microspheres, 8 mg of fluorescent amine, and 2 mg of diamine were suspended in 50 milliliters of water. The pH was adjusted to 12 with 1.0N NaOH, and the mixture was allowed to stir overnight at room temperature. Under these reaction conditions, the methyl ester and hydroxyethyl ester groups can be replaced by forming covalent bonds with the amine moieties through a transacylation reaction as described in March, Advanced Organic Chemistry: Reactions, Mechanisms, and Structure, 2nd edition 1977, pp. 386–87. As set out in this reference, the conversion of esters to amides is a useful reaction, and unsubstituted, N-substituted, and N,N-disubstituted amides can be prepared in this way from the appropriate amine. The ester group may be alkyl or aryl, although for convenience the ester group will generally contain from one to ten carbon atoms.

The resulting microspheres were dialyzed against deionized water, pH 9.0 for 5 days, changed two to three times daily to remove the unconjugated dansyl cadaverine and diamine.

The resulting microspheres remain in single suspension, without clumping.

The extent of conjugation was estimated by incorporation of radioactive ethanolamine under the foregoing conditions. The number of covalently bound dansylcadaverine markers was estimated to be 0.005 micromoles per milliliter of solution.

The average size of the microspheres was determined by electron microscopy to be 310 angstroms in diameter, and the number of dansylcadaverine markers covalently attached per microsphere was determined by calculation to be approximately 14,400. This corresponds to about 5,000,000 molecules of dansylcadaverine per square micrometer on the surface of the average fluorescent microsphere. This is far above the minimum of 1,000 molecules per square micrometer generally regarded as necessary for visualizing microspheres by fluorescent microscopy. The density of fluorescent moieties bound to the microsphere is many times that of previously known microspheres.

The microspheres were found to be individually easily observable by fluorescent microscopy at a magnification of 630× to 1,000×.

The resulting fluorescent microspheres were found to be remarkably stable for periods of more than one year.

EXAMPLE 3

Attachment of Antibody to Fluorescent Microspheres

Fluorescent microspheres produced in accordance with Example 2 were covalently conjugated to the well-established anti-H-2K monoclonal antibody following a two step glutaraldehyde reaction in accordance with the method described by Rembaum and Dreyer, *Science*, 208, pp. 364–68 (1980). The activation of the beads with glutaraldehyde must be carried out shortly before the are coupled to the antibody.

A mixture was formed consisting of 0.6 mg of spheres suspended in one ml water per 0.1 ml of 50% glutaraldehyde. The mixture was stirred overnight to react the free amino group of the aminododecyl-amido-linked microspheres with the glutaraldehyde. Excess glutaraldehyde was removed by extensive dialysis.

The anti-H-2K antibody was grown in serum-free media, to prevent contamination with albumin, which has been found to bind to the bead. The antibody is used in the form of supernatant in Dulbecco's (modified) MEM in serum-free media supplemented with 1.5 mg oxalacetate, 0.5 mg insulin, 3.5 mg transferrin, 0.12 ug ethanolamine and 0.043 ug sodium selenite per liter of DMEM. One ml of unpurified antibody (about 0.1 microgram) was added per 6 mg of microspheres to the glutaraldehyde-activated microspheres. The resulting mixture was stirred for 16 hours at 4° C. before glycine was added to react with the remaining unconjugated aldehyde groups. The mixture was layered on a discontinuous sucrose density gradient (60% w/w overlayered with 10-20%) in phosphate buffered saline (PBS), pH 7.4, and spun in a Spinco SW 10.1 rotor ultracentrifuge for one hour at 35,000 rpm. The antibody-microsphere conjugates were recovered at the 20-60% interface and dialyzed overnight against PBS, pH 7.4.

The antibody-microsphere conjugates were found to be primarily in single suspension, with no visible large aggregates or clumps of microspheres.

EXAMPLE 4

Use of Antibody/Fluorescent Microspheres To Visualize Cell Surface Antigens

The binding specificity of the antibody-microspheres was determined by incubation with three groups of splenocytes. The first group carried the H-$2^d$ antigen, the second lacked the relevant H-$2^d$ antigen, and the third carried the H-$2^d$ antigen but was preincubated with free monoclonal antibody. The second and third groups served as controls. Following thirty minutes' incubation at room temperature, cells were washed twice with PBS (pH 7.4) and then scored for fluorescence under a Leit Ortholux fluorescent microscope with an A filter combination consisting of 340-380 mu for excitation and 430 mu for emission at a magnification of 630× to 1,000×. A minimum of one hundred cells per group were scored.

When Do4 or Do9 containing fetal bovine serum were used for conjugation under various conditions, the binding efficiency was in the range of 40-60% for group 1 and 14-20% for group 2. By polyacrylamide gel electrophoresis, abundant albumin (more than 98%) was found in supernatant containing bovine serum. Conjugation experiments using albumin alone showed that albumin not only binds to microspheres but also to the cell surface, and thus decreases substantially the antigen-specific binding. An alternative monoclonal antibody (Do4.7) secreted in serum-free media was prepared for the study. Eighty-eight percent, 27% and 4% of binding specificity was detected in group 1, 2 and 3 respectively. However, the 27% binding in the negative control prompted optimizing the method in the following manner:

1. With various concentration of antibody (Ab) to 1 ml of fluorescent microspheres (6 mg/ml) using 1 hour reaction time for conjugation, the maximal binding specificity was obtained using 0.3 ml of Do4.7 antibody per 1 ml of fluorescent microspheres. However, the 20% range of non-specific binding in group 2 remains. This may be caused by inefficient binding of immunoglobulin, thereby allowing the fluorescent microspheres to bind to the cell surface non-specifically.

2. By studying the time effect on efficiency of the immunoglobulin binding to fluorescent microspheres (0.25 ml of Do4.7 antibody per 1 ml of fluorescent microspheres), the optimal condition to achieve the maximal covalent binding of antibody to fluorescent microspheres was determined to be a four hour reaction. The maximal binding specificity to group 1 is 88% while the non-specific binding for group 2 is reduced to 10-11%.

EXAMPLE 5

Attachment of Avidin to Fluorescent Microspheres

Avidin was attached to the microspheres of Example 2 by a glutaraldehyde reaction similar to that used in Example 3.

A mixture was formed consisting of 2.4 mg of spheres suspended in four ml water per 0.4 ml of 50% glutaraldehyde. The mixture was incubated for one hour to react the free amino group of the aminododecyl-amido-linked microspheres with the glutaraldehyde. Excess glutaraldehyde was removed by extensive dialysis, overnight against PBS pH 7.4. The glutaraldehyde activated microspheres were concentrated down to 1 ml by using Centricon-30, followed by gently mixing the 1 ml microsphere with 200 ul (1 mg/1 ml) streptavidin for four hours. At the end of four hours, 1 mg of lysine was added and further mixed for an additional hour to react with the remaining unconjugated aldehyde groups.

The mixture was layered on a discontinuous sucrose density gradient (60% w/w overlayed with 10-20%) in 1.0M NaCl, 0.01M EDTA pH 8.5 and spun in a Spinco SW 50.1 rotor ultracentrifuge for one hour at 35,000 rpm. The avidin-microsphere conjugates were recovered at the 20-60% interface and dialyzed overnight against 1.0M NaCl, 0.01M EDTA, pH 8.5.

The avidin-microsphere conjugates showed no tendency to clump into visible aggregates. Electron microscopic examination of the beads showed primarily single beads, with occasional groups of two to four beads.

To determine the presence of reactive avidin on the fluorescent microspheres, the avidin fluoromicrosphere complexes were spotted on a nitrocellulose paper in a serial dilution and were detected using a commercially available alkaline phosphatase colorimetric method produced by Bethesda Research Laboratories. It was found that the complex can be detected in a hundred-fold dilution, as compared with a negative control.

EXAMPLE 6

Use of Avidin/Fluorescent Microspheres To Detect Single Gene Sequences in Plasmid DNA The specificity of the microspheres produced in accordance with Example 5 for the purpose of detecting gene sequences was determined as follows. Plasmid DNA encoding the N-myconcogene sequences was first linearized using a restriction enzyme (Eco R1) and denatured. The DNA sequences were then labeled with biotin-16-dUTP using the oligolabeling method of Feinberg and Vogelstein, *Anal. Biochem.*, 132, pp. 6-13 (1983). The biotinylated plasmid DNA was incubated with the avidin/fluoromicrosphere for one hour. The resulting conjugates of DNA-biotin-avidin-microspheres was examined under an electron microscope. It is estimated that more than 175 biotin molecules per thousand base pairs were incorporated. Following denaturation, the single stranded plasmid DNA encoding N-myc oncogene sequences labeled with biotin-16-dUTP therefore serves as a DNA probe.

EXAMPLE 7

Use of Avidin/Fluorescent Microspheres To Detect Single Gene Sequences Via Southern Blot The avidin/fluorescent microspheres of Example 5 may be utilized in a modification of the standard Southern blot procedure, as described for example in Davis, Dibney and Battey, "Basic Methods In Molecular Biology" (Elsevier 1986), pp. 62–65, to detect gene sequences fluorimetrically, rather than radiochemically as in the standard Southern blot procedure.

DNA is extracted from lymphocytes or fibroblast cultures and cleaved with restriction endonucleases at specific sequences. The resulting DNA fragments are separated by gel electrophoresis on the basis of their molecular weight. The size of the fragments can therefore be determined by calibrating the gel with a known size standard. The DNA fragments are then transferred from their position in an agarose gel to a nitrocellulose filter placed directly above the gel. The DNA is denatured, neutralized and transferred in a high-salt buffer by capillary action. The resulting single-stranded DNA binds to the filter and is permanently bonded by baking the filter. This procedure is well known and is described in "Basic Methods In Molecular Biology" supra, pp. 41–61. The bonded DNA is later hybridized to a biotinylated probe as in Example 6, by the method of Feinberg and Vogelstein, supra, to detect hybridizing species. This is followed by incubation with the avidin/fluoromicrospheres of Example 5 onto the nitrocellulose paper for one hour with polylysine. The presence of the probe (the known DNA sequences) can be detected instantly by visualization of the fluorescence when exposed to a portable UV light, or the fluorescence can be quantitated by a spectrofluorometer.

EXAMPLE 8

Use of Avidin/Fluorescent Microspheres To Detect Gene Sequences Via In Situ Hybridization to the DNA of Chromosomes As described in the foregoing Examples, single stranded plasmid DNA encoding N-myc or ribosomal gene sequences, or any other gene sequences of interest, labeled with biotin-16-dUTP can be utilized to detect gene sequences via in situ hybridization as follows.

Chromosomes obtained from neuroblastoma cell line, or any other tissues such as lymphocyte and fibroblast, can be first identified with Quinacrine staining (so-called Q-banding) under fluorescence microscopy using the proper filter combinations. In a Leitz fluorescent microscope, H filter combination is used for Quinacrine. Metaphase cells showing Q banding are photographed and their coordinates recorded. The slides are destained and ready to be used for in situ hybridization.

The method used for in situ hybridization may follow that of Harper and Saunders, *Chromosoma*, 83, pp 431-39 (1981), with certain modifications. After thorough washing to remove Q staining, slides of fixed metaphase chromosomes are subjected to the following: removal of endogenous RNA by incubating with ribonucleases; denaturing of chromosomal DNA; hybridization by incubating the previously labeled biotinylated DNA probe on the slide overnight; incubation of the slide with avidin/fluoromicrospheres; examination of fluorescent microspheres attached consistently to the location of a specific chromosome. The final step is done by first relocating the previously recorded Q-banded chromosome and then detecting the presence of fluoromicrospheres under fluorescent microscopy using A filter (a filter used for examining dansyl fluorescence) and correlating the frequent occurrence of the fluoromicrospheres on a specific location of the previously identified chromosome, thereby mapping the gene to a specific chromosome.

EXAMPLE 9

Use of Antibody/Colored Microspheres To Visualize Cell Surface Antigens

Beads similar to those of Example 2 were formed by substituting Rhodamine B (N-(9-(2-Carboxyphenyl)-6-(diethylamino)-3H-xanthen-3-ylidene)-N-ethylethanaminium chloride) for dansyl cadaverine. Monoclonal antibody Do4.7 was bonded to these beads by the methods of Examples 3 and 4, and binding specificity was determined by the method of Example 4. The dyed beads were visible by light microscopy. The markers were even more distinctly visible under UV excitation. Binding specificity was 80%. Higher specificity may be achieved by pre-reacting Rhodamine B isothiocyanate with cadaverine by the method of R. C. Nairn, supra, Chapter 2, pages 5–38, and Appendix, pages 369–72.

EXAMPLE 10

Use of Microspheres To Detect Carcinoembryonic Antigen

Monoclonal antibody 7H10C3 to carcinoembryonic antigen (CEA) was bonded to the beads of Example 2 by the methods of Examples 3 and 4. Carcinoembryonic antigen was spotted on a nitrocellulose test strip in serial dilutions. When incubated with a suspension of the dyed beads, visible color change occurred to a dilution of about 0.001 nanograms per microliter under ultraviolet light.

It will be seen from the foregoing examples that the present invention provides fluorescent microspheres which are smaller than previously known fluorescent microspheres, yet which are more intensely fluorescent than even much larger microspheres. They thus permit visualization of far more precisely defined areas of a substrate than previously possible, permit far brighter marking of closely related sites, permit direct localization of cell surface antigens without a secondary antibody, and permit conjugation of DNA to fluorescent microspheres by taking advantage of the strong non-covalent interaction between avidin and biotin. The microspheres may be made with various fluorochromes which include primary amine groups. They are chemically stable for long periods in single suspension. They are thus versatile tools with wide applications for the detection of minute quantities of biological substances via rapid, simple, safe and highly sensitive methodology.

Numerous variations, within the scope of the appended claims, will be apparent to those skilled in the art in light of the foregoing description. For example, automated techniques such as flow cytometry, may be used with the beads. Other fluorescent dyes may be utilized, and visible light dyes such as brilliant cresyl blue may also be used. These dyes are preferably, but not necessarily, attached to spacers. They are added in excess (70-90% dye) with the diamine spacers. Biotin may be added to the diamine reactive groups via other means such as N-hydrosuccinimido biotin or by photochemical means, for reaction with avidinated probes, or in a sandwich reaction. These variations are merely illustrative.

I claim:

1. A fluorescent marker system comprising a plurality of fluorescent microspheres, each fluorescent microsphere comprising an acrylic latex bead having a diameter of less than 500 angstroms, said bead having conjugated, by transacylation of ester terminations on the surface of said bead, (a) at least 5,000 fluorescent molecules, and (b) spacer arms and specific binding means attached to said spacer arms for attaching said microspheres to biological analytes.

2. The marker system of claim 1 wherein said beads have a diameter of from 200 to 400 angstroms.

3. The marker system of claim 1 wherein said beads have at least 10,000 fluorescent molecules conjugated per bead.

4. The marker system of claim 3 wherein said fluorescent molecules are conjugated to said beads by carbon chains having a length of from two to ten carbons.

5. The marker system of claim 1 wherein said beads are primarily in single suspension in an aqueous medium.

6. The marker system of claim 5 wherein said spacer arms comprise carbon chains having a length of from eight to twenty carbons.

7. A dyed microsphere comprising an acrylic latex bead having a diameter of less than 500 angstroms, at least 5,000 dye marker means conjugated to the surface of said bead by transacylation of ester terminations on the surface of said bead for rendering said bead individually visible by microscopy, a plurality of spacer arms attached to said bead by transacylation of ester terminations on the surface of said bead, and specific binding means on said spacer arms for binding specifically with a biological analyte to label said biological analyte.

8. The microsphere of claim 7 wherein said specific binding means is chosen from the group consisting of avidin and biotin.

9. The microsphere of claim 7 wherein said specific binding means comprise antibodies.

10. A method of identifying a site on a biological analyte, said method comprising a step of reacting with said site a fluorescent acrylic latex microsphere having a diameter of less than 500 angstroms and at least 5,000 fluorescent markers conjugated to the microsphere by transcylation of ester terminations on the surface of said microsphere, and at least one species conjugated to the microsphere through a spacer arm by transacylation of ester terminations on the surface of said microsphere, said species having a specific affinity for said binding site, and a step of detecting said individual microsphere by fluorescence microscopy.

11. The method of claim 10 wherein said step of detecting said individual microsphere is by human observation.

12. The method of claim 10 wherein the fluorescent markers are conjugated to said microsphere by carbon chains having a length of from two to ten carbons.

13. The method of claim 10 wherein said spacer arms comprise carbon chains having a length of from eight to twenty carbons.

14. The method of claim 10 wherein the species having a specific affinity for said binding site is chosen from the group consisting of avidin and biotin.

15. The method of claim 10 wherein the species having a specific affinity for said binding site is an antibody.

* * * * *

UNITED STATES PATENT AND TRADEMARK OFFICE
CERTIFICATE OF CORRECTION

PATENT NO. : 5,132,242

DATED : July 21, 1992

INVENTOR(S) : Sau W. Cheung

It is certified that error appears in the above-identified patent and that said Letters Patent is hereby corrected as shown below:

Col. 2, line 11 is "the carboxylic acid group.s" should be --bromide reaction, and the secondary antibody was conjugated to the carboxylic acid groups.--;

Col. 4, line 19 is "of the beads is not spacers." should be --of the beads is not affected by the addition of the fluorescent markers and the spacers.--;

Col. 6, line 68 is "before the are" should be --before they are--.

Signed and Sealed this

Seventh Day of September, 1993

Attest:

BRUCE LEHMAN

Attesting Officer

Commissioner of Patents and Trademarks